(12) United States Patent
Uchiyama et al.

(10) Patent No.: US 7,687,030 B2
(45) Date of Patent: Mar. 30, 2010

(54) HYDROGEN GAS VISUALIZATION DEVICE

(75) Inventors: Naoki Uchiyama, Hamamatsu (JP); Hiroyuki Matsumoto, Hamamatsu (JP)

(73) Assignee: Kabushiki Kaisha ATSUMITEC, Hamamatsu-shi (JP)

( * ) Notice: Subject to any disclaimer, the term of this patent is extended or adjusted under 35 U.S.C. 154(b) by 698 days.

(21) Appl. No.: 11/581,553

(22) Filed: Oct. 16, 2006

(65) Prior Publication Data

US 2007/0084726 A1 Apr. 19, 2007

(30) Foreign Application Priority Data

Oct. 17, 2005 (JP) ............................. 2005-301713

(51) Int. Cl.
*G01N 30/96* (2006.01)
(52) U.S. Cl. .................. 422/88; 436/113; 436/144; 436/147; 73/23.2; 73/31.05; 73/31.06
(58) Field of Classification Search ............ 422/88; 436/144, 147, 113; 73/23.2, 31.05, 31.06
See application file for complete search history.

(56) References Cited

U.S. PATENT DOCUMENTS

| | | | |
|---|---|---|---|
| 6,596,236 B2 * | 7/2003 | DiMeo et al. | 422/88 |
| 2003/0169476 A1 * | 9/2003 | Yoshimura | 359/265 |
| 2004/0037740 A1 | 2/2004 | Liu et al. | |
| 2005/0169807 A1 | 8/2005 | Carpenter et al. | |

FOREIGN PATENT DOCUMENTS

| | | |
|---|---|---|
| EP | 1 345 071 A | 9/2003 |
| JP | 05-196569 A | 8/1993 |
| JP | 08-129008 A | 5/1996 |
| JP | 2002-181808 A | 6/2002 |
| JP | 2003-335553 A | 11/2003 |
| JP | 2004-139134 A | 5/2004 |
| JP | 2005-83832 A | 3/2005 |
| WO | WO 2005/078434 A2 | 8/2005 |

\* cited by examiner

*Primary Examiner*—Bruce F Bell
(74) *Attorney, Agent, or Firm*—Frishauf, Holtz, Goodman & Chick, P.C.

(57) ABSTRACT

A hydrogen gas visualization device comprises a hydrogen sensor having a thin film layer formed on the surface of a substrate and a catalyst layer formed on the surface of the thin film layer which, when contacted by hydrogen gas contained in an atmosphere, hydrogenates the thin film layer and thereby changes the optical reflectance of the thin film layer, and one or more sensor faces provided with the hydrogen sensor. The hydrogen gas visualization device visualizes, on the sensor faces, the distribution of hydrogen gas contained in the atmosphere contacting the hydrogen sensor and thereby visualizes the existence and flow of the hydrogen gas.

4 Claims, 4 Drawing Sheets

HYDROGEN GAS VISUALIZATION DEVICE

BACKGROUND OF THE INVENTION

1. Field of the Invention

This invention relates to a hydrogen gas visualization device for visualizing the existence of hydrogen gas in an atmosphere to allow it to be recognized by the eye or the like.

2. Description of the Related Art

In order to suppress the emission of carbon dioxide, attention is given to hydrogen as an energy source. If, however, hydrogen gas leaks into an atmosphere around a device using hydrogen as an energy source (automobile using hydrogen-fuel cells, for example) or the like (atmosphere at a basement car park, a hydrogen gas station or the like), an explosion may happen. Thus, it is necessary to quickly detect and stop the leakage of hydrogen gas. It is however not practical to detect the hydrogen gas leaked into the atmosphere using the Schlieren method, the PIV method and the like, which are gas detection methods for use in laboratories and the like. In the first place, these methods can detect a convective flow of gas but cannot selectively detect hydrogen gas among other gases.

Thus, a leaked hydrogen gas detection device employing a semiconductor sensor using tin oxide capable of selectively detecting hydrogen gas in an atmosphere has been devised.

Further, switchable mirror glass which selectively reacts to hydrogen gas in the manner such that a thin film layer formed on the glass surface is hydrogenated at room temperature (around 20° C.) under the action of a catalyst layer and comes into a transparent state, and is dehydrogenated in the temperature range of the room temperature to 100° C. and comes into a mirror state is proposed in Japanese Unexamined Patent Publication No. 2003-335553 (hereinafter referred to as "patent document 1"), Japanese Unexamined Patent Publication No. 2004-139134 (hereinafter referred to as "patent document 2"), etc.

Such switchable mirror glass is applied to windows in buildings and automobiles to perform light control by changing the optical transparency of the glass almost uniformly across the entire glass surface, using hydrogen gas.

Further, a detection device which, by using a hydrogen sensor including a thin film layer formed on the surface of a substrate such as a glass or vinyl sheet, capable of being quickly hydrogenated under the action of a catalyst layer and thereby changing in optical reflectance, can detect the existence of hydrogen gas at a location where the hydrogen sensor is placed is proposed in Japanese Unexamined Patent Publication No. 2005-83832 (hereinafter referred to as "patent document 3").

In order to, however, prevent the leaked hydrogen gas from causing an explosion, quick detection of the leakage is not enough. It is necessary to quickly identify the source from which the hydrogen gas leaks and stop the leakage of the hydrogen gas. For this purpose, it is necessary to be able to detect the existence and flow of the leaked hydrogen gas across a relatively large region, safely and quickly, and determine the leakage source from the flow of the leaked hydrogen gas.

The semiconductor sensor using tin oxide capable of selectively detecting hydrogen gas, however, operates at relatively high temperature around 400° C. and therefore needs a heating device. Thus, if such semiconductor sensor is applied to a leaked hydrogen gas detection device, the possibility of the heating device inducing an explosion of leaked hydrogen gas cannot be denied. Further, since a power source is required to operate the semiconductor sensor, the possibility of failure of a power-source device or the like inducing an explosion of leaked hydrogen gas cannot be denied. There is also a problem that if a disaster or the like causes a power outage, the operation of the hydrogen gas detection device stops. Further, the above-mentioned hydrogen gas detection device only detects the existence of leaked hydrogen gas at a location where the semiconductor sensor is placed, and cannot quickly detect a flow of leaked hydrogen gas across a relatively large region and therefore cannot quickly identify the leakage source from which hydrogen gas leaks.

Further, the above-mentioned switchable mirror glass (patent documents 1 and 2) selectively reacting to hydrogen is intended to be changed in optical transparency by hydrogen gas almost uniformly across the entire glass surface, and therefore not suited to quickly detect a flow of leaked hydrogen gas across a relatively large region.

Further, the hydrogen sensor with a catalyst layer formed on the surface of a substrate of glass or the like (patent document 3) only detects the existence of hydrogen gas at a location where the sensor is placed. It cannot visualize the existence and flow of hydrogen gas in an atmosphere.

SUMMARY OF THE INVENTION

An aspect of the present invention is a hydrogen gas visualization device comprising: a hydrogen sensor having a substrate, a thin film layer formed on the surface of the substrate, and a catalyst layer formed on the surface of the thin film layer which, when contacted by hydrogen gas contained in an atmosphere, hydrogenates the thin film layer and thereby changes the optical reflectance of the thin film layer; and one or more sensor faces provided with the hydrogen sensor, wherein the hydrogen gas visualization device visualizes, on the sensor faces, the distribution of hydrogen gas contained in the atmosphere contacting the hydrogen sensor and thereby visualizes the existence and flow of the hydrogen gas.

BRIEF DESCRIPTION OF THE DRAWINGS

The present invention will become more fully understood from the detailed description given hereinafter and the accompanying drawings which are given by way of illustration only, and thus, are not limitative of the present invention, and wherein.

DETAILED DESCRIPTION OF THE PREFERRED EMBODIMENTS

Figure 1:
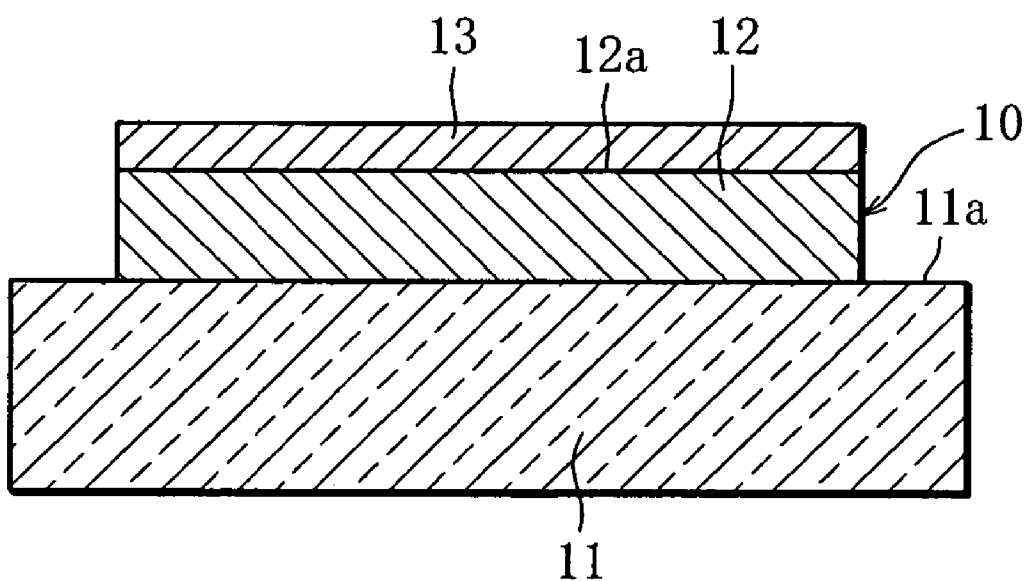
FIG. 1 shows a cross-sectional structure of a hydrogen sensor used in hydrogen gas visualization devices according to embodiments of the present invention.

Referring to the drawings, hydrogen gas visualization devices according to embodiments of the present invention will be described.

A hydrogen gas visualization device according to a first embodiment of the present invention will be described on the basis of FIGS. 1, 2A, 2B, 3A and 3B.

First, referring to FIG. 1, an example of a hydrogen sensor used in this embodiment will be described. A hydrogen sensor 10 shown in FIG. 1 includes a substrate 11 of metal, glass, acrylic resin, polyethylene resin (polyethylene sheet or polyethylene film) or the like. On the surface 11a of this substrate 11, a thin film layer 12 of magnesium-nickel alloy or magnesium is formed. On the surface 12a of the thin film layer 12, a catalyst layer 13 of palladium or platinum is formed.

The thin film layer 12 can be formed by the sputtering method, the vacuum deposition method, the electron-beam deposition method, the electroplating method or the like, and the composition thereof is MgNi$_x$ ($0 \leq x < 0.6$), for example. The catalyst layer 13 can be formed, for example by coating the surface 12a of the thin film layer 12, and the thickness thereof is 1 nm to 100 nm. If the hydrogen sensor 10 provided with such thin film layer 12 and catalyst layer 13 contacts an atmosphere of hydrogen concentration about 100 ppm to 1% or higher, a visible (visualizable) quick change in optical reflectance occurs in the region of the thin film layer 12 which has contacted such atmosphere, for example in several to 10 seconds or so.

The composition of the thin film layer 12 and the method used to form it are not limited to those mentioned above, as long as they can provide such thin film layer that is quickly hydrogenated under the action of the catalyst layer 13 and quickly changes in optical reflectance when the catalyst layer 13 contacts hydrogen gas. Also the composition and thickness of the catalyst layer 13 and the method used to form it are not limited to those mentioned above. It is to be noted that the above-mentioned optical reflectance should be read as the optical reflectance with regard to visible light when observation by the eye is intended, but is not limited to the optical reflectance with regard to visible light when monitoring is performed using an infrared camera or the like, for example.

Figure 2A:
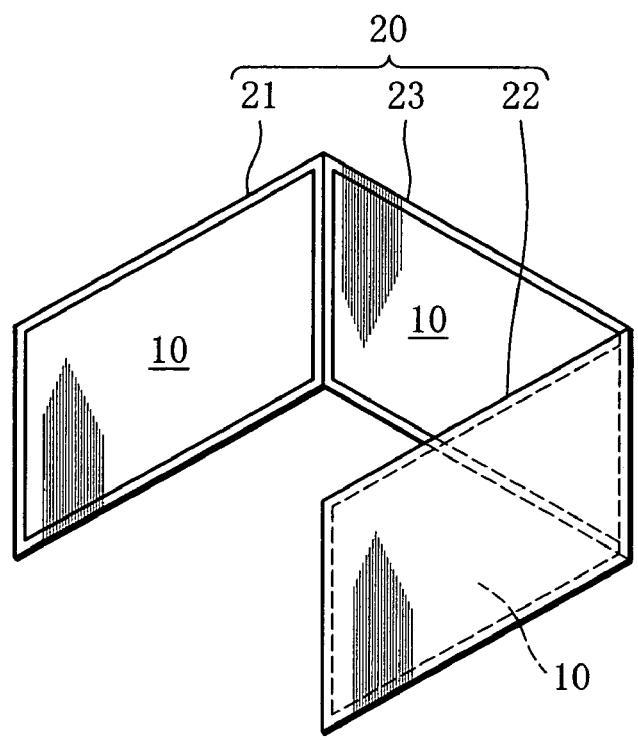
FIG. 2A shows an example of schematic structure of a hydrogen gas visualization device (first embodiment) using the hydrogen sensor shown in FIG. 1.
Figure 2B:
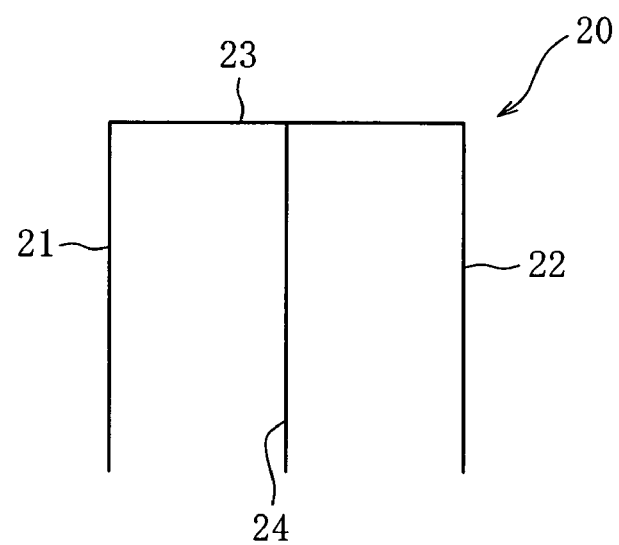
FIG. 2B shows an example of modification to the hydrogen gas visualization device shown in FIG. 2A.

FIGS. 2A and 2B are diagrams showing examples of schematic structure for a hydrogen gas visualization device 20 using the hydrogen sensor 10 shown in FIG. 1. The hydrogen gas visualization device 20 is installed and used, for example in a car park such as a basement car park for automobiles using hydrogen as fuel (hereinafter referred to as "hydrogen-fueled cars"), and as shown in FIG. 2A, includes a first side face 21, a second side face 22 and a rear face 23 which form sensor faces. A space defined by the first side face 21, second side face 22 and rear face 23 forms a parking space in which a hydrogen-fueled car is parked. Here, the front side opposite to the rear face 23 is open to provide an entryway for an hydrogen-fueled car to go in and out. Thus, when the hydrogen gas visualization device 20 is installed in a car park, the first side face 21, second side face 22 and rear face 23 are positioned to surround a parked hydrogen-fueled car on three sides, leaving an entryway for the hydrogen-fueled car to go in and out.

Further, as shown in FIG. 2B, by dividing the parking space with a partition 24 arranged parallel to the first and second side faces 21, 22, parking spaces for more than one hydrogen-fueled cars can be provided.

In the hydrogen gas visualization device 20 shown in FIG. 2A, the hydrogen sensor 10 is attached to each of the first side face 21, second side face 22 and rear face 23 to cover the almost entire parking-space-side surface of each. In the hydrogen gas visualization device 20 shown in FIG. 2B, the hydrogen sensor 10 is also attached to either surface of the partition 24. If necessary, these hydrogen gas visualization devices 20 may have a ceiling (sensor face) with the hydrogen sensor 10 attached to cover the almost entire lower surface thereof.

It is to be noted that the hydrogen sensor covering the almost entire surface of each face may be either a single hydrogen sensor or consist of a plurality of hydrogen sensors.

Here, suppose that in a basement car park with the hydrogen gas visualization devices 20 shown in FIG. 2A installed, a hydrogen-fueled car is parked with its back directed to the rear face 23 of the hydrogen gas visualization device 20. If hydrogen gas leaks from the back of the hydrogen-fueled car, the leaked hydrogen gas reaches the rear face 23 and moves upward along the surface of the rear face 23, so that in the region contacted by this flow of the leaked hydrogen gas, the optical reflectance of the thin film layer 12 decreases. Accordingly, in the region in which the optical reflectance has decreased, reflection of illumination light for the basement car park or the like on the surface of the hydrogen sensor 10 changes. Thus, the hydrogen gas visualization device 20 can visualize the distribution and flow of the leaked hydrogen gas.

Figure 3A:
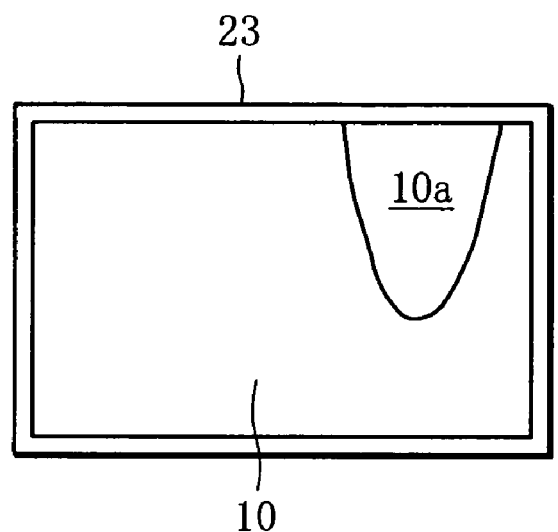
FIG. 3A shows an example of change in the optical reflectance of a thin film layer at the surface of the hydrogen sensor used in the hydrogen gas visualization device shown in FIG. 2A.
Figure 3B:
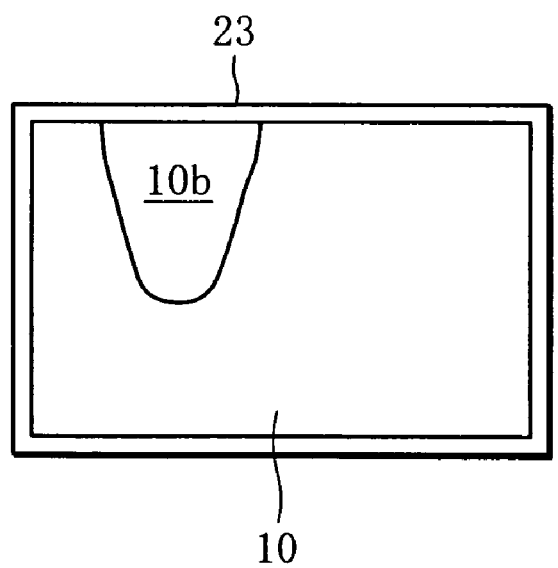
FIG. 3B shows another example of change in the optical reflectance of the thin film layer at the surface of the hydrogen sensor used in the hydrogen gas visualization device shown in FIG. 2A.

FIGS. 3A and 3B are diagrams showing examples of change in the optical reflectance of the thin film layer 12 at the surface of the hydrogen sensor 10 attached to the rear face 23. If a decrease in the optical reflectance of the thin film layer 12 of the hydrogen sensor 10 occurs in an approximately upper-right region 10a of the rear face 23 of the hydrogen gas visualization device 20 (FIG. 3A), it indicates that the hydrogen-gas leakage source is near the right side of the rear face 23. Since the optical reflectance of the thin film layer 12 decreases corresponding to the concentration of the leaked hydrogen gas, a location showing a great decrease in optical reflectance is near the hydrogen-gas leakage source. Naturally, optical fluctuations are generated in the region 10a in accordance with changes in the leaked hydrogen gas flow. If a decrease in the optical reflectance of the thin film layer 12 of the hydrogen sensor 10 occurs in an approximately upper-left region 10b of the rear face 23 of the hydrogen gas visualization device 20 as shown in FIG. 3B, it indicates that the hydrogen-gas leakage source is near the left side of the rear face 23 of the hydrogen-gas visualization device 20.

As described above, the hydrogen gas visualization device 20 visualizes the distribution and flow of leaked hydrogen gas which has contacted the surface of the hydrogen sensor 10, through change in the optical reflectance of the thin film layer 12. Thus, provided that the hydrogen gas visualization device 20 is illuminated with illumination light for the basement car park or the like, hydrogen gas leakage and the location of the leakage can be recognized from change in reflected light. Naturally, the hydrogen gas visualization device 20 may detect changes in the optical reflectance of the thin film layer 12 of the hydrogen sensor 10, in reflection of outdoor natural light, not artificial light such as illumination light.

The hydrogen gas visualization device 20 may be arranged such that the first side face 21, second side face 22 and rear face 23 (sensor faces) are made of, for example, glass or transparent plastic, and that the hydrogen sensor 10 using a transparent polyethylene sheet or the like for the substrate 11 is attached to each of these sensor faces. In this case, if, as shown in FIG. 3A or 3B, leaked hydrogen gas contacts the hydrogen sensor 10 in the region 10a or 10b and causes a change in optical reflectance, the distribution and flow of the leaked hydrogen gas can be observed by the eye from outside the hydrogen gas visualization device 20, because of change in optical reflectance in the region 10a or 10b.

Needless to say, leaked hydrogen gas can be visualized also when any or all of the first side face 21, second side face 22 and rear face 23 of the hydrogen gas visualization device 20 are not flat faces but curved faces.

Further, the number of the sensor faces and the three-dimensional configuration of the sensor faces combined can be changed appropriately in accordance with need.

Figure 4:
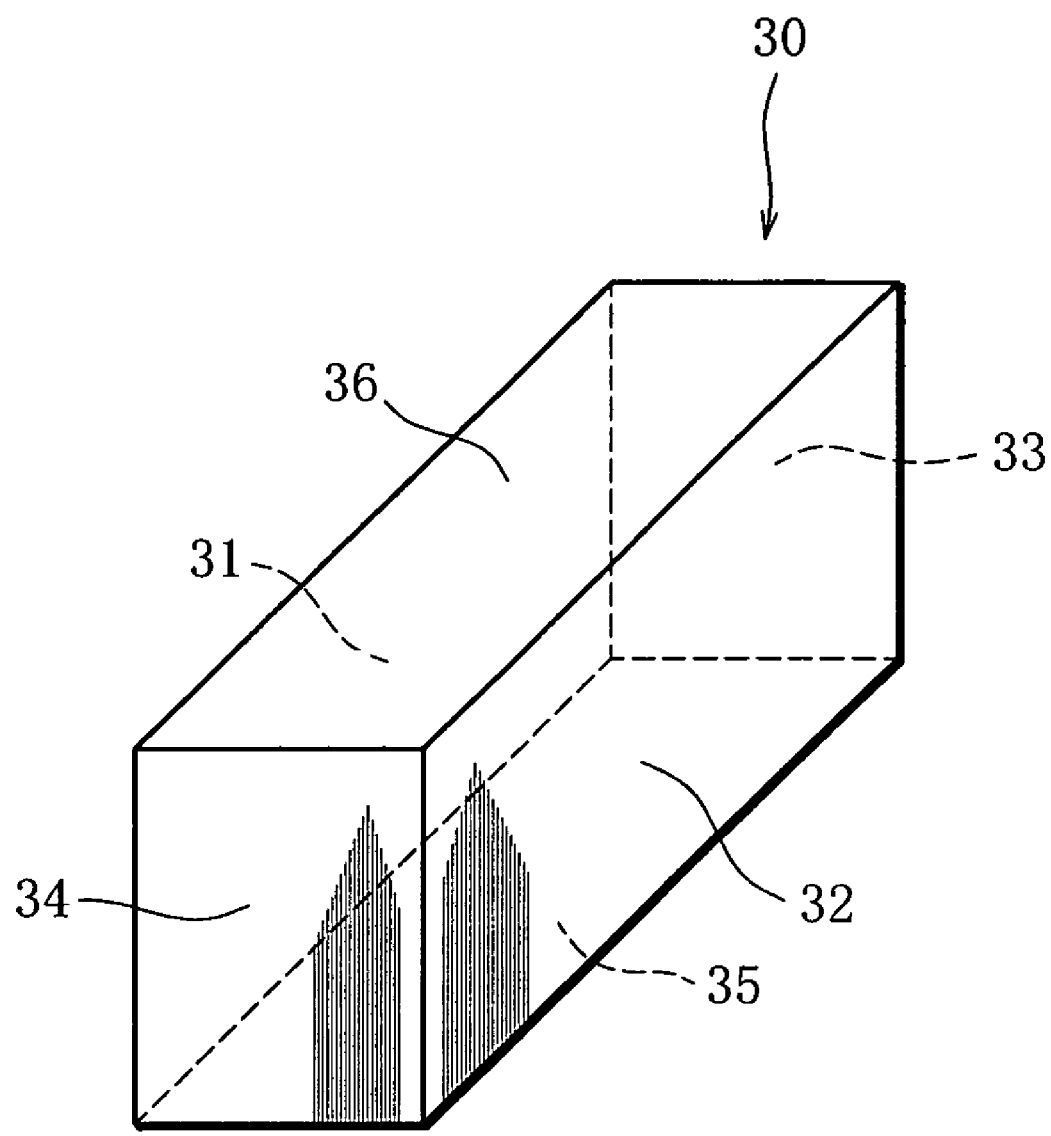
FIG. 4 shows a schematic structure of a hydrogen gas visualization device according to a second embodiment of the present invention.

Next, referring to FIG. 4, a hydrogen gas visualization device according to a second embodiment of the present invention will be described.

It is to be noted that components of which functional counterparts are found in the first embodiment will be referred to by the same reference signs, while the description thereof will be omitted. A hydrogen gas visualization device 30 is a hexahedron (cuboid) comprising a first side face 31, a second side face 32, a rear face 33, a front face 34, a bottom face 35 and a top face 36, which are made of transparent plastic or the like and form sensor faces. To each of the first side face 31, second side face 32, rear face 33, front face 34, bottom face 35 and top face 36, a hydrogen sensor 10 using a transparent polyethylene sheet or the like for a substrate 11 is attached or stuck to cover the almost entire surface of each that faces an internal space. The hydrogen gas visualization device 30 is arranged such that any of the faces (front face 34, for example) can be opened and closed to allow, for example, a hydrogen gas storage device to be placed in the internal space.

Also in this case, the hydrogen sensor covering the almost entire surface of each face may be either a single hydrogen sensor or consist of a plurality of hydrogen sensors.

If hydrogen gas leaks from the hydrogen gas storage device contained in the hydrogen gas visualization device 30, the leaked hydrogen gas is detected by one of the hydrogen sensors 10 attached to the six faces composing the hydrogen gas visualization device 30. The optical reflectance of the thin film layer 12 of that sensor 10 changes depending on the concentration of the leaked hydrogen gas, and in the region in which the optical reflectance changes, optical fluctuations are caused by the flow of the leaked hydrogen gas. Thus, the distribution and flow of the leaked hydrogen gas can be visualized, and the location at which the hydrogen gas leaks from the hydrogen gas storage device can be recognized. Naturally, what is contained in the hydrogen gas visualization device 30 is not limited to the hydrogen gas storage device but may be a hydrogen-fuel cell, a hydrogen production device or the like.

Also in this second embodiment, the number of the sensor faces and the three-dimensional configuration of the sensor faces combined can be changed appropriately in accordance with need.

It is to be noted that the hydrogen gas visualization devices 20, 30 are not limited to devices for detecting and visualizing leaked hydrogen gas. They may be, for example, experimental devices for simulating a hydrogen gas flow (wind channel, etc., for example).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A hydrogen gas visualization device comprising:
a plurality of hydrogen sensors, each comprising: a substrate, a thin film layer formed on a surface of the substrate, and a catalyst layer formed on a surface of the thin film layer, wherein the catalyst layer, when contacted by hydrogen gas contained in an atmosphere, hydrogenates the thin film layer and thereby changes an optical reflectance of the thin film layer;
wherein a plurality of sensor faces are formed by the hydrogen sensors,
wherein the hydrogen gas visualization device visualizes, on the sensor faces, a distribution of hydrogen gas contained in the atmosphere contacting the hydrogen sensor and thereby visualizes the existence and flow of the hydrogen gas, and
wherein the sensor faces are three-dimensionally combined to surround a potential hydrogen-gas leakage source.

2. The hydrogen gas visualization device according to claim 1, wherein the thin film layer is a thin film layer of magnesium-nickel alloy or magnesium.

3. The hydrogen gas visualization device according to claim 1, wherein the catalyst layer contains palladium or platinum.

4. The hydrogen gas visualization device according to claim 1, wherein the catalyst layer is 1 nm to 100 nm in thickness.

* * * * *